United States Patent
Vanderlende et al.

(10) Patent No.: US 9,902,790 B2
(45) Date of Patent: Feb. 27, 2018

(54) PRODUCING POLYOLEFIN PRODUCTS

(71) Applicant: Univation Technologies, LLC, Houston, TX (US)

(72) Inventors: Daniel D. Vanderlende, Sugar Land, TX (US); C. Jeff Harlan, Houston, TX (US); Haiqing Peng, Sugar Land, TX (US); Michael D. Awe, Langhorne, PA (US); Roger L. Kuhlman, Lake Jackson, TX (US); Ching-Tai Lue, Sugar Land, TX (US); Timothy R. Lynn, Glen Gardner, NJ (US); Wesley R. Mariott, Manvel, TX (US); Daniel P. Zilker, Jr., Charleston, WV (US)

(73) Assignee: Univation Technologies, LLC, Houston, TX (US)

(*) Notice: Subject to any disclaimer, the term of this patent is extended or adjusted under 35 U.S.C. 154(b) by 0 days.

(21) Appl. No.: 15/117,789

(22) PCT Filed: Feb. 10, 2015

(86) PCT No.: PCT/US2015/015141
§ 371 (c)(1),
(2) Date: Aug. 10, 2016

(87) PCT Pub. No.: WO2015/123177
PCT Pub. Date: Aug. 20, 2015

(65) Prior Publication Data
US 2017/0022309 A1  Jan. 26, 2017

Related U.S. Application Data

(60) Provisional application No. 61/938,466, filed on Feb. 11, 2014, provisional application No. 61/938,472, filed on Feb. 11, 2014, provisional application No. 61/981,291, filed on Apr. 18, 2014, provisional application No. 61/985,151, filed on Apr. 28, 2014, provisional application No. 62/032,383, filed on Aug. 1, 2014, provisional application No. 62/087,905, filed on Dec. 5, 2014, provisional application No. 62/087,914, filed on Dec. 5, 2014, provisional application No. 62/088,196, filed on Dec. 5, 2014, (Continued)

(51) Int. Cl.
| | |
|---|---|
| *C08F 4/653* | (2006.01) |
| *C08F 4/6592* | (2006.01) |
| *C08L 23/08* | (2006.01) |
| *C08F 210/16* | (2006.01) |
| *C08F 4/659* | (2006.01) |
| *C07F 17/00* | (2006.01) |
| *C08F 210/02* | (2006.01) |
| *C08F 4/76* | (2006.01) |
| *C08F 210/14* | (2006.01) |
| *C08F 210/08* | (2006.01) |

(52) U.S. Cl.
CPC ............ *C08F 210/16* (2013.01); *C07F 17/00* (2013.01); *C08F 4/65904* (2013.01); *C08F 4/76* (2013.01); *C08F 210/02* (2013.01); *C08F 4/65912* (2013.01); *C08F 4/65916* (2013.01); *C08F 4/65925* (2013.01); *C08F 4/65927* (2013.01); *C08F 210/08* (2013.01); *C08F 210/14* (2013.01); *C08F 2410/02* (2013.01); *C08F 2420/00* (2013.01); *C08F 2420/01* (2013.01); *C08F 2500/01* (2013.01); *C08F 2500/02* (2013.01); *C08F 2500/08* (2013.01); *C08F 2500/09* (2013.01); *C08F 2500/10* (2013.01); *C08F 2500/11* (2013.01); *C08F 2500/12* (2013.01); *C08F 2500/13* (2013.01); *C08F 2500/18* (2013.01); *C08F 2800/20* (2013.01); *C08L 23/0815* (2013.01)

(58) Field of Classification Search
CPC ... C08F 4/65904; C08F 4/65912; C08L 23/08
See application file for complete search history.

(56) References Cited

U.S. PATENT DOCUMENTS

| | | | |
|---|---|---|---|
| 6,943,227 B2 | 9/2005 | Ishihama et al. | |
| 7,763,561 B2 | 7/2010 | McDaniel et al. | |
| 8,288,487 B2 | 10/2012 | Yang et al. | |

(Continued)

FOREIGN PATENT DOCUMENTS

| | | |
|---|---|---|
| JP | 2003105029 | 4/2003 |
| JP | 2009126902 | 6/2009 |

(Continued)

OTHER PUBLICATIONS

International Search Report & Written Opinion for related PCT Application PCT/US2015/015141, dated May 29, 2015 (7 pgs).

*Primary Examiner* — Caixia Lu
(74) *Attorney, Agent, or Firm* — Brooks, Cameron & Huebsch, PLLC

(57) ABSTRACT

A method of polymerizing olefins is disclosed. The method comprises contacting ethylene and at least one comonomer with a catalyst system to produce a polyolefin polymer that is multimodal. The catalyst system comprises a first catalyst that promotes polymerization of the ethylene into a low molecular weight (LMW) portion of the polyolefin polymer and a second catalyst that promotes polymerization of the ethylene into a high molecular weight (HMW) portion of the polyolefin polymer. The first catalyst and at least a portion of the second catalyst are co-supported to form a commonly-supported catalyst system and at least a portion of the second catalyst is added as a catalyst trim feed to the catalyst system.

13 Claims, 3 Drawing Sheets

Related U.S. Application Data provisional application No. 62/087,911, filed on Dec. 5, 2014.

(56) References Cited

U.S. PATENT DOCUMENTS

| | | |
|---|---|---|
| 8,664,140 B2 | 3/2014 | Schmitz et al. |
| 8,859,451 B2 | 10/2014 | Mihan et al. |
| 8,932,975 B2 | 1/2015 | Yang et al. |
| 8,999,875 B2 | 4/2015 | Fantinel et al. |
| 9,346,896 B2 | 5/2016 | McDaniel et al. |
| 2009/0240010 A1 | 9/2009 | McDaniel et al. |
| 2010/0076167 A1 | 3/2010 | McDaniel et al. |
| 2010/0317904 A1 | 12/2010 | Small et al. |
| 2012/0010375 A1 | 1/2012 | Yang et al. |
| 2012/0046428 A1* | 2/2012 | Kao ........................ C08F 10/00 526/113 |
| 2012/0059134 A1 | 3/2012 | Yang et al. |

FOREIGN PATENT DOCUMENTS

| | | |
|---|---|---|
| WO | 99/03897 | 1/1999 |
| WO | 0109200 | 2/2001 |
| WO | 03027131 | 4/2003 |
| WO | 2009067201 | 5/2009 |
| WO | 2009082451 | 7/2009 |

\* cited by examiner

PRODUCING POLYOLEFIN PRODUCTS

RELATED APPLICATIONS

This application is a National Stage Application under 35 U.S.C. § 371 of International Application Number PCT/US2015/015141, filed Feb. 10, 2015 and published as WO 2015/123177 on Aug. 20, 2015, which claims the benefit to the following U.S. Provisional Applications 61/938,472, filed Feb. 11, 2014; 61/938,466, filed Feb. 11, 2014; 61/981,291, filed Apr. 18, 2014; 61/985,151, filed Apr. 28, 2014; 62/032,383, filed Aug. 1, 2014; 62/088,196, filed Dec. 5, 2014; 62/087,914, filed Dec. 5, 2014; 62/087,911, filed Dec. 5, 2014; 62/087,905, filed Dec. 5, 2014; the entire contents of which are incorporated herein by reference in its entirety.

BACKGROUND

Ethylene alpha-olefin (polyethylene) copolymers are typically produced in a low pressure reactor, utilizing, for example, solution, slurry, or gas phase polymerization processes. Polymerization takes place in the presence of catalyst systems such as those employing, for example, a Ziegler-Natta catalyst, a chromium based catalyst, a metallocene catalyst, or combinations thereof.

A number of catalyst compositions containing single site, e.g., metallocene, catalysts have been used to prepare polyethylene copolymers, producing relatively homogeneous copolymers at good polymerization rates. In contrast to traditional Ziegler-Natta catalyst compositions, single site catalyst compositions, such as metallocene catalysts, are catalytic compounds in which each catalyst molecule contains one or only a few polymerization sites. Single site catalysts often produce polyethylene copolymers that have a narrow molecular weight distribution. Although there are single site catalysts that can produce broader molecular weight distributions, these catalysts often show a narrowing of the molecular weight distribution (MWD) as the reaction temperature is increased, for example, to increase production rates. Further, a single site catalyst will often incorporate comonomer among the molecules of the polyethylene copolymer at a relatively uniform rate.

It is generally known in the art that a polyolefin's MWD will affect the different product attributes. Polymers having a broad molecular weight distribution may have improved physical properties, such as stiffness, toughness, processability, and environmental stress crack resistance (ESCR), among others. To achieve these properties, bimodal polymers have become increasingly important in the polyolefins industry, with a variety of manufacturers offering products of this type. Whereas older technology relied on two-reactor systems to generate such material, advances in catalyst design and supporting technology have allowed for the development of single-reactor bimetallic catalyst systems capable of producing bimodal high density polyethylene (HDPE). These systems are attractive both from a cost perspective and ease of use.

The composition distribution of an ethylene alpha-olefin copolymer refers to the distribution of comonomer, which form short chain branches, among the molecules that comprise the polyethylene polymer. When the amount of short chain branches varies among the polyethylene molecules, the resin is said to have a "broad" composition distribution. When the amount of comonomer per 1000 carbons is similar among the polyethylene molecules of different chain lengths, the composition distribution is said to be "narrow".

The composition distribution is known to influence the properties of copolymers, for example, stiffness, toughness, extractable content, environmental stress crack resistance, and heat sealing, among other properties. The composition distribution of a polyolefin may be readily measured by methods known in the art, for example, Temperature Raising Elution Fractionation (TREF) or Crystallization Analysis Fractionation (CRYSTAF).

It is generally known in the art that a polyolefin's composition distribution is largely dictated by the type of catalyst used and is typically invariable for a given catalyst system. Ziegler-Natta catalysts and chromium based catalysts produce resins with broad composition distributions (BCD), whereas metallocene catalysts normally produce resins with narrow composition distributions (NCD).

Resins having a broad orthogonal composition distribution (BOCD) in which the comonomer is incorporated predominantly in the high molecular weight chains can lead to improved physical properties, for example toughness properties and environmental stress crack resistance (ESCR). Because of the improved physical properties of resins with orthogonal composition distributions needed for commercially desirable products, there exists a need for controlled techniques for forming polyethylene copolymers having a broad orthogonal composition distribution.

Control of these properties is obtained for the most part by the choice of the catalyst system. Thus, the catalyst design is important for producing polymers that are attractive from a commercial standpoint. Because of the improved physical properties of polymers with the broad molecular distributions needed for commercially desirable products, there exists a need for controlled techniques for forming polyethylene copolymers having a broad molecular weight distribution.

SUMMARY

A method of polymerizing olefins is disclosed. The method comprises contacting ethylene and at least one comonomer with a catalyst system to produce a polyolefin polymer that is multimodal. The catalyst system comprises a first catalyst that promotes polymerization of the ethylene into a low molecular weight (LMW) portion of the polyolefin polymer and a second catalyst that promotes polymerization of the ethylene into a high molecular weight (HMW) portion of the polyolefin polymer. The first catalyst and at least a portion of the second catalyst are co-supported to form a commonly-supported catalyst system and at least a portion of the second catalyst is added as a catalyst trim feed to the catalyst system. Polymers made by the methods herein are also disclosed.

DETAILED DESCRIPTION

Figure 1:
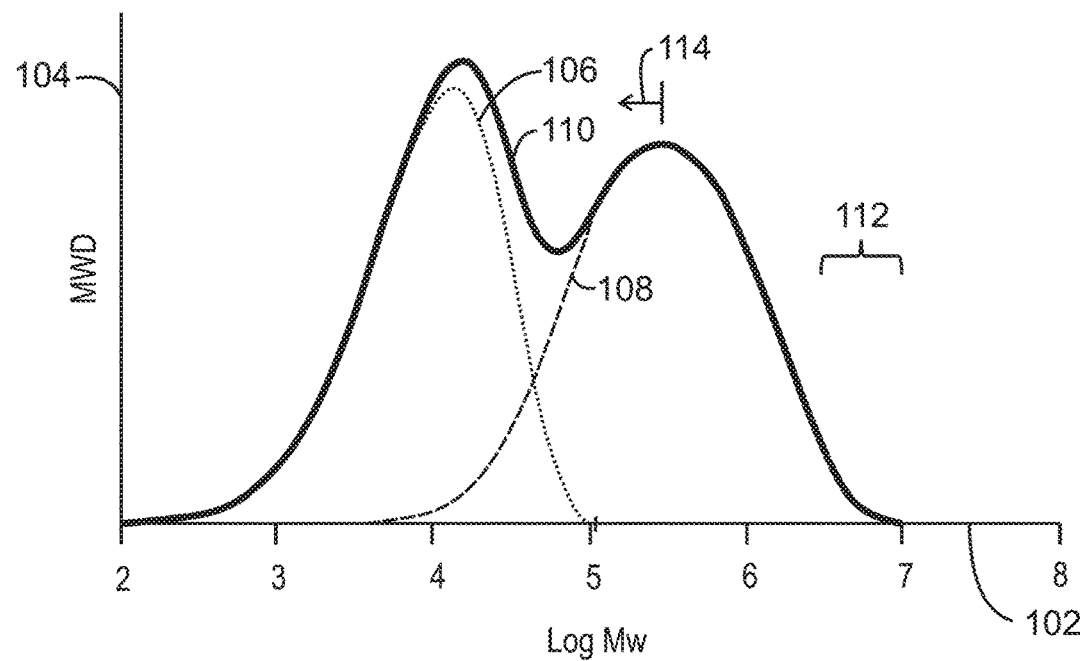
FIG. 1 is a representative plot of molecular weight distribution of polyolefin polymerized with a two catalyst system that includes a first metallocene catalyst and a second metallocene catalyst, in accordance with embodiments described herein.

The melt flow ratio (MFR) of a polyethylene is the ratio of melt indexes, $I_{21}/I_2$, and is an important property to be able to control in polymerization methods. In polymerization methods using multiple catalysts, such as a dual catalyst system comprising a HMW catalyst species and a LMW catalyst species, it is known that MFR may be controlled using trim addition of the LMW catalyst species.

The methods disclosed herein utilize a commonly-supported catalyst system with trim addition of the HMW catalyst species, rather than the LMW catalyst species. Specifically, the methods comprise contacting ethylene and at least one comonomer with a catalyst system to produce a polyolefin polymer that is multimodal. The catalyst system comprises a first catalyst that promotes polymerization of the ethylene into a low molecular weight (LMW) portion of the polyolefin polymer and a second catalyst that promotes polymerization of the ethylene into a high molecular weight (HMW) portion of the polyolefin polymer. The first catalyst and at least a portion of the second catalyst are co-supported to form a commonly-supported catalyst system and at least a portion of the second catalyst is added as a catalyst trim feed to the catalyst system.

The catalyst system useful in these methods may be formulated with a higher than typically desired amount of LMW catalyst species, and then MFR may be controlled via trim addition of additional HMW catalyst species. It is believed that the methods disclosed herein facilitate better mixing of the polymer LMW and HMW fractions being polymerized, and thus they surprisingly result in a reduction in polymer gels. Moreover, without wishing to be bound by theory, it is believed that when the HMW catalyst species is used as the trim catalyst, a HMW polymer shell may beneficially form on the polymer particle, which may improve extrusion properties and contribute to the reduction in gels. Exemplary data demonstrating these effects is provided herein.

Herein, the modifiers "LMW" and "HMW" of "LMW catalyst species" and "HMW catalyst species," respectively, refer to the contribution of the catalyst to the polymer molecular weight in polymerization, and do not refer to the molecular weight of the catalysts themselves.

The methods disclosed herein may be used with a variety of different catalysts. A useful HMW catalyst species may comprise bis(n-propylcyclopentadienyl) Hafnium dimethyl, referred to herein as "HfP" for convenience. A useful LMW catalyst species may comprise meso and/or rac entantiomers of di(1-ethylindenyl) zirconium dimethyl, referred to herein as "EthInd" or "1 EtInd2ZrMe2" for convenience. Thus, in the methods herein, the first catalyst may be a LMW catalyst species such as EthInd in a slurry or other form, driving polymerization of a LMW fraction or portion of the polyethylene polymer. The second catalyst may be a HMW catalyst species such as HfP in a solution or other form, driving polymerization of the HMW fraction or portion of the polyethylene polymer. At least a portion of the second catalyst or HMW catalyst species is co-deposited on a support prior to entering the reactor, with additional HMW catalyst species added as trim to control MFR and/or other properties of the polymer.

As indicated, the two catalysts may be co-supported on a catalyst support to form a commonly supported catalyst system prior to flowing the catalyst to the polymerization reactor. The catalysts may be co-supported on a single common support or co-supported on multiple common supports. Additionally, the catalysts and methods disclosed herein may be used with a variety of reactor arrangements, for example, single-reactor or multiple-reactor polymerization systems.

The commonly supported catalyst system may be characterized by an initial co-deposit on a mol fraction basis of the second catalyst to the first catalyst. As used herein, "initial co-deposit on a mol fraction basis of the second catalyst to the first catalyst" refers to the relative amounts of the second catalyst and the first catalyst that are initially co-deposited on the common support. For example, an initial co-deposit on a mol fraction basis of the second catalyst to the first catalyst of 0.6:0.4 means that 0.6 mol of second catalyst are co-deposited on the common support for every 0.4 mol of first catalyst deposited on the common support. The initial co-deposit on a mol fraction basis of the second catalyst to the first catalyst may range from, for example, 0.01:0.99 to 0.99:0.01, 0.1:0.9 to 0.9:0.1, 0.2:0.8 to 0.8:0.2, 0.7:0.3 to 0.3:0.7, 0.4:0.6 to 0.6:0.4, or 0.55:0.45 to 0.45:0.55, or be about 0.6:0.4 or about 0.5:0.5.

The amount of additional HMW catalyst species that may be added as trim per gram of the dry co-supported catalyst (i.e. the weight of catalyst prior to being slurried) may range from 1.8 µmol to 150 µmol, 3.6 µmol to 120 µmol, 6.2 µmol to 90 µmol, 12.4 µmol to 75 µmol, or 25 µmol to 50 µmol.

The methods disclosed herein may enable the formation of polymers with an improved balance of properties, such as stiffness, toughness, processability, and environmental stress crack resistance. Such a balance of properties can be achieved, for example, by controlling the amounts and types of catalysts present on the support. Selection of the catalysts and ratios may be used to adjust the MWD of the polymer produced. The MWD can be controlled by combining catalysts giving the desired weight average molecular weight (MW) and individual molecular weight distributions of the produced polymer. For example, a typical MWD for linear metallocene polymers is 2.5 to 3.5. Blend studies indicate it would be desirable to broaden this distribution by employing mixtures of catalysts that each provide different average molecular weights. In such cases, the ratio of the weight average molecular weight or the number average molecular weight for a low molecular weight component of the polymer and a high molecular weight component of the polymer could be between 1:1 and 1:10, or about 1:2 and 1:5, for instance.

Appropriate selection of the catalysts and ratios may be used to adjust not just the MWD, but also the short chain branch distribution (SCBD) and long-chain branch distribution (LCBD) of the polymer, for example, to provide a polymer with a broad orthogonal composition distribution (BOCD). The MWD, SCBD, and LCBDs would be controlled by combining catalysts with the appropriate weight average MW, comonomer incorporation, and long chain branching (LCB) formation under the conditions of the polymerization.

The density of a polyethylene copolymer provides an indication of the incorporation of comonomer into a polymer, with lower densities indicating higher incorporation. The difference in the densities of the LMW component and the HMW component may be greater than about 0.02 g/cm3, or greater than about 0.04 g/cm3, with the HMW component having a lower density than the LMW component. These factors can be adjusted by controlling the MWD and SCBD, which, in turn, can be adjusted by changing the relative amounts of the pre-catalysts on the support. This may be adjusted during the formation of the pre-catalysts or by adding one of the components as trim. Feedback of polymer property data can be used to adjust the amount of catalyst added as trim.

Further, a variety of resins with different MWD, SCBD, and LCBD may be prepared from a limited number of catalysts. To perform this function, the pre-catalysts should trim well onto activator supports. Two parameters that benefit this are solubility in alkane solvents and rapid supportation on the catalyst slurry en-route to the reactor. This favors the use of MCNs to achieve controlled MWD, SCBD, and LCBD. Techniques for selecting catalysts that can be used to generate targeted molecular weight compositions, including BOCD polymer systems, are disclosed herein.

FIG. 1 is a plot 100 of molecular weight distributions for a polyolefin polymer produced by a two catalyst system that includes first and second catalysts, in accordance with embodiments described herein. In the plot 100, the x-axis 102 represents the log of the MW, and the y-axis 104 represents the MWD. Each of the catalysts can be selected to contribute a certain molecular weight component. For example, a catalyst, such as EthInd, the meso and rac entantiomers of which are shown as structures (I-A) and (I-B) respectively below, may be selected to produce a low molecular weight component 106. Another catalyst, such as HfP, shown as structure (II) below, may be selected to produce a higher molecular weight component 108. In one or more embodiments, catalysts such as those shown in structures (IV-C), (IV-D), (V-A), and (V-B) may be utilized. Of course, other metallocene catalysts or non-metallocene catalysts, as described herein, may be selected, a few of which are also shown below. The individual molecular weight components form a single MWD curve 110 for the polymer. The particular metallocene or non-metallocene catalysts selected may depend on the desired downstream applications of the formed polymer resins, such as for film, blow-molding applications, pipe applications, and so on.

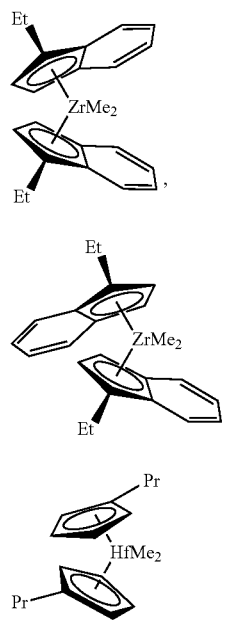

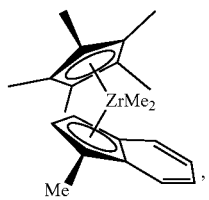

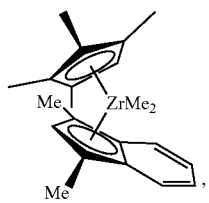

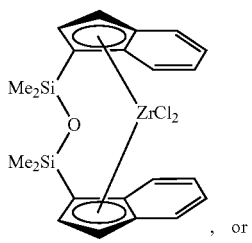

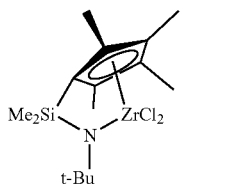

The polymer produced may include polyethylene that is multimodal. For example, the polyethylene may be bimodal and have chains formed via a polymerization catalyst system having a low molecular weight (LMW) species catalyst and a high molecular weight (HMW) species catalyst that are co-supported to give a commonly supported catalyst system, and wherein at least a portion of the HMW species catalyst is a catalyst trim. In some instances, the polyethylene is a copolymer of ethylene and an alpha olefin comonomer having from 4 to 20 carbon atoms.

Various catalyst systems and components may be used to generate the polymers and molecular weight compositions disclosed. These are discussed in the sections to follow. The first section discusses catalyst compounds that can be used in embodiments. The second section discusses generating catalyst slurries that may be used for implementing the techniques described. The third section discusses catalyst supports that may be used. The fourth section discusses catalyst activators that may be used. The fifth section discusses the catalyst component solutions that may be used to add additional catalysts in trim systems. Gas phase polymerizations may use static control or continuity agents, which are discussed in the sixth section. A gas-phase polymerization reactor with a trim feed system is discussed in the seventh section. The use of the catalyst composition to control product properties is discussed in an eighth section and an exemplary polymerization process is discussed in a ninth section. Examples of the implementation of the procedures discussed are incorporated into a tenth section.

Catalyst Compounds
Metallocene Catalyst Compounds

Metallocene catalyst compounds may be used in the methods herein. Metallocene catalyst compounds include "half sandwich" and/or "full sandwich" compounds having one or more Cp ligands (cyclopentadienyl and ligands isolobal to cyclopentadienyl) bound to at least one Group 3 to Group 12 metal atom, and one or more leaving group(s) bound to the at least one metal atom. As used herein, all reference to the Periodic Table of the Elements and groups thereof is to the NEW NOTATION published in HAWLEY'S CONDENSED CHEMICAL DICTIONARY, Thirteenth Edition, John Wiley & Sons, Inc., (1997) (reproduced there with permission from IUPAC), unless reference is made to the Previous IUPAC form noted with Roman numerals (also appearing in the same), or unless otherwise noted.

The Cp ligands are one or more rings or ring system(s), at least a portion of which includes π-bonded systems, such as cycloalkadienyl ligands and heterocyclic analogues. The ring(s) or ring system(s) typically include atoms selected from the group consisting of Groups 13 to 16 atoms, and, in a particular exemplary embodiment, the atoms that make up the Cp ligands are selected from the group consisting of carbon, nitrogen, oxygen, silicon, sulfur, phosphorous, germanium, boron, aluminum, and combinations thereof, where carbon makes up at least 50% of the ring members. In a more particular exemplary embodiment, the Cp ligand(s) are selected from the group consisting of substituted and unsubstituted cyclopentadienyl ligands and ligands isolobal to cyclopentadienyl, non-limiting examples of which include cyclopentadienyl, indenyl, fluorenyl and other structures. Further non-limiting examples of such ligands include cyclopentadienyl, cyclopentaphenanthreneyl, indenyl, benzindenyl, fluorenyl, octahydrofluorenyl, cyclooctatetraenyl, cyclopentacyclododecene, phenanthrindenyl, 3,4-benzofluorenyl, 9-phenylfluorenyl, 8-H-cyclopent[a]acenaphthylenyl, 7-H-dibenzofluorenyl, indeno[1,2-9]anthrene, thiophenoindenyl, thiophenofluorenyl, hydrogenated versions thereof (e.g., 4,5,6,7-tetrahydroindenyl, or "H4 Ind"), substituted versions thereof (as discussed and described in more detail below), and heterocyclic versions thereof.

The metal atom "M" of the metallocene catalyst compound can be selected from the group consisting of Groups 3 through 12 atoms and lanthanide Group atoms; selected from the group consisting of Groups 3 through 10 atoms; selected from the group consisting of Sc, Ti, Zr, Hf, V, Nb, Ta, Mn, Re, Fe, Ru, Os, Co, Rh, Ir, and Ni; selected from the group consisting of Groups 4, 5, and 6 atoms; selected from the group consisting of Ti, Zr, Hf atoms; and selected from Zr or Hf. The oxidation state of the metal atom "M" can range from 0 to +7 in one exemplary embodiment; and in a more particular exemplary embodiment, can be +1, +2, +3, +4, or +5; and in yet a more particular exemplary embodiment can be +2, +3 or +4. The groups bound to the metal atom "M" are such that the compounds described below in the formulas and structures are electrically neutral, unless otherwise indicated. The Cp ligand forms at least one chemical bond with the metal atom M to form the "metallocene catalyst compound." The Cp ligands are distinct from the leaving groups bound to the catalyst compound in that they are not highly susceptible to substitution/abstraction reactions.

The one or more metallocene catalyst compounds can be represented by the structure (VI):

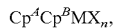

in which M is as described above; each X is chemically bonded to M; each Cp group is chemically bonded to M; and n is 0 or an integer from 1 to 4, and either 1 or 2 in a particular exemplary embodiment.

The ligands represented by $Cp^A$ and $Cp^B$ in structure (VI) can be the same or different cyclopentadienyl ligands or ligands isolobal to cyclopentadienyl, either or both of which can contain heteroatoms and either or both of which can be substituted by a group R. In at least one specific embodiment, $Cp^A$ and $Cp^B$ are independently selected from the group consisting of cyclopentadienyl, indenyl, tetrahydroindenyl, fluorenyl, and substituted derivatives of each.

Independently, each $Cp^A$ and $Cp^B$ of structure (VI) can be unsubstituted or substituted with any one or combination of substituent groups R. Non-limiting examples of substituent groups R as used in structure (VI) as well as ring substituents in structures discussed and described below, include groups selected from the group consisting of hydrogen radicals, alkyls, alkenyls, alkynyls, cycloalkyls, aryls, acyls, aroyls, alkoxys, aryloxys, alkylthiols, dialkylamines, alkylamidos, alkoxycarbonyls, aryloxycarbonyls, carbamoyls, alkyl- and dialkyl-carbamoyls, acyloxys, acylaminos, aroylaminos, and combinations thereof. More particular non-limiting examples of alkyl substituents R associated with structures herein include methyl, ethyl, propyl, butyl, pentyl, hexyl, cyclopentyl, cyclohexyl, benzyl, phenyl, methylphenyl, and tert-butylphenyl groups and the like, including all their isomers, for example, tertiary-butyl, isopropyl, and the like.

As used herein, and in the claims, hydrocarbyl substituents, or groups, are made up of between 1 and 100 or more carbon atoms, the remainder being hydrogen. Non-limiting examples of hydrocarbyl substituents include linear or branched or cyclic: alkyl radicals; alkenyl radicals; alkynyl radicals; cycloalkyl radicals; aryl radicals; alkylene radicals, or a combination thereof. Non-limiting examples include methyl, ethyl, propyl, butyl, pentyl, hexyl, cyclopentyl, cyclohexyl; olefinically unsaturated substituents including vinyl-terminated ligands (for example but-3-enyl, prop-2-enyl, hex-5-enyl and the like), benzyl or phenyl groups and the like, including all their isomers, for example tertiary butyl, isopropyl, and the like.

As used herein, and in the claims, substituted hydrocarbyl substituents, or groups, are made up of between 1 and 100 or more carbon atoms, the remainder being hydrogen, fluorine, chlorine, bromine, iodine, oxygen, sulfur, nitrogen, phosphorous, boron, silicon, germanium or tin atoms or other atom systems tolerant of olefin polymerization systems. Substituted hydrocarbyl substituents are carbon based radicals. Non-limiting examples of substituted hydrocarbyl substituents trifluoromethyl radical, trimethylsilanemethyl (Me3SiCH 2-) radicals.

As used herein, and in the claims, heteroatom substituents, or groups, are fluorine, chlorine, bromine, iodine, oxygen, sulfur, nitrogen, phosphorous, boron, silicon, germanium or tin based radicals. They may be the heteroatom atom by itself. Further, heteroatom substituents include organometalloid radicals. Non-limiting examples of heteroatom substituents include chloro radicals, fluoro radicals, methoxy radicals, diphenyl amino radicals, thioalkyls, thioalkenyls, trimethylsilyl radicals, dimethyl aluminum radicals, alkoxydihydrocarbylsilyl radicals, siloxydiydrocabylsilyl radicals, tris(perflourophenyl)boron and the like.

Other possible radicals include substituted alkyls and aryls such as, for example, fluoromethyl, fluroethyl, difluoroethyl, iodopropyl, bromohexyl, chlorobenzyl, hydrocarbyl substituted organometalloid radicals including trimethylsilyl, trimethylgermyl, methyldiethylsilyl, and the like, and halocarbyl-substituted organometalloid radicals, including tris(trifluoromethyl)silyl, methylbis(difluoromethyl)silyl, bromomethyldimethylgermyl and the like; and disubstituted boron radicals including dimethylboron, for example; and disubstituted Group 15 radicals including dimethylamine, dimethylphosphine, diphenylamine, methylphenylphosphine, as well as Group 16 radicals including methoxy, ethoxy, propoxy, phenoxy, methylsulfide and ethylsulfide. Other substituent groups R include, but are not limited to, olefins such as olefinically unsaturated substituents including vinyl-terminated ligands such as, for example, 3-butenyl, 2-propenyl, 5-hexenyl, and the like. In one exemplary embodiment, at least two R groups (two adjacent R groups in a particular exemplary embodiment) are joined to form a ring structure having from 3 to 30 atoms selected from the group consisting of carbon, nitrogen, oxygen, phosphorous, silicon, germanium, aluminum, boron, and combinations thereof. Also, a substituent group R such as 1-butanyl can form a bonding association to the element M.

Each leaving group, or X, in the structure (VI) above and for the structure (VII) below is independently selected from the group consisting of: halogen ions, hydrides, C1 to C12 alkyls, C2 to C12 alkenyls, C6 to C12 aryls, C7 to C20 alkylaryls, C1 to C12 alkoxys, C6 to C16 aryloxys, C7 to C8 alkylaryloxys, C1 to C12 fluoroalkyls, C6 to C12 fluoroaryls, and C1 to C12 heteroatom-containing hydrocarbons and substituted derivatives thereof, in a more particular exemplary embodiment; hydride, halogen ions, C1 to C6 alkyls, C2 to C6 alkenyls, C7 to C18 alkylaryls, C1 to C6 alkoxys, C6 to C14 aryloxys, C7 to C16 alkylaryloxys, C1 to C6 alkylcarboxylates, C1 to C6 fluorinated alkylcarboxylates, C6 to C12 arylcarboxylates, C7 to C18 alkylarylcarboxylates, C1 to C6 fluoroalkyls, C2 to C6 fluoroalkenyls, and C7 to C18 fluoroalkylaryls in yet a more particular exemplary embodiment; hydride, chloride, fluoride, methyl, phenyl, phenoxy, benzoxy, tosyl, fluoromethyls and fluorophenyls, in yet a more particular exemplary embodiment; C1 to C12 alkyls, C2 to C12 alkenyls, C6 to C12 aryls, C7 to C20 alkylaryls, substituted C1 to C12 alkyls, substituted C6 to C12 aryls, substituted C7 to C20 alkylaryls and C1 to C12 heteroatom-containing alkyls, C1 to C12 heteroatom-containing aryls, and C1 to C12 heteroatom-containing alkylaryls, in yet a more particular exemplary embodiment; chloride, fluoride, C1 to C6 alkyls, C2 to C6 alkenyls, C7 to C18 alkylaryls, halogenated C1 to C6 alkyls, halogenated C2 to C6 alkenyls, and halogenated C7 to C18 alkylaryls, in yet a more particular exemplary embodiment; chloride, methyl, ethyl, propyl, phenyl, methylphenyl, dimethylphenyl, trimethylphenyl, fluoromethyls (mono-, di- and trifluoromethyls) and fluorophenyls (mono-, di-, tri-, tetra- and pentafluorophenyls), in yet a more particular exemplary embodiment.

Other non-limiting examples of X groups include amides, amines, phosphines, ethers, carboxylates, dienes, hydrocarbon radicals having from 1 to 20 carbon atoms, fluorinated hydrocarbon radicals (e.g., —C6F5 (pentafluorophenyl)), fluorinated alkylcarboxylates (e.g., CF3C(O)O—), hydrides, halogen ions and combinations thereof. Other examples of X ligands include alkyl groups such as cyclobutyl, cyclohexyl, methyl, heptyl, tolyl, trifluoromethyl, tetramethylene, pentamethylene, methylidene, methyoxy, ethyoxy, propoxy, phenoxy, bis(N-methylanilide), dimethylamide, dimethylphosphide radicals and the like. In one exemplary embodiment, two or more X's form a part of a fused ring or ring system. In at least one specific embodiment, X can be a leaving group selected from the group consisting of chloride ions, bromide ions, C1 to C10 alkyls, and C2 to C12 alkenyls, carboxylates, acetylacetonates, and alkoxides.

The metallocene catalyst compound includes those of structure (VI) where $Cp^A$ and $Cp^B$ are bridged to each other by at least one bridging group, (A), such that the structure is represented by structure (VII):

$Cp^A(A)Cp^BMX_n$.

These bridged compounds represented by structure (VII) are known as "bridged metallocenes." The elements $Cp^A$, $Cp^B$, M, X and n in structure (VII) are as defined above for structure (VI); where each Cp ligand is chemically bonded to M, and (A) is chemically bonded to each Cp. The bridging group (A) can include divalent hydrocarbon groups containing at least one Group 13 to 16 atom, such as, but not limited to, at least one of a carbon, oxygen, nitrogen, silicon, aluminum, boron, germanium, tin atom, and combinations thereof; where the heteroatom can also be C1 to C12 alkyl or aryl substituted to satisfy neutral valency. In at least one specific embodiment, the bridging group (A) can also include substituent groups R as defined above (for structure (VI)) including halogen radicals and iron. In at least one specific embodiment, the bridging group (A) can be represented by C1 to C6 alkylenes, substituted C1 to C6 alkylenes, oxygen, sulfur, R'2C=, R'2Si=, =Si(R')2Si(R'2)=, R'2Ge=, and R'P=, where "=" represents two chemical bonds, R' is independently selected from the group consisting of hydride, hydrocarbyl, substituted hydrocarbyl, halocarbyl, substituted halocarbyl, hydrocarbyl-substituted organometalloid, halocarbyl-substituted organometalloid, disubstituted boron, disubstituted Group 15 atoms, substituted Group 16 atoms, and halogen radical; and where two or more R' can be joined to form a ring or ring system. In at least one specific embodiment, the bridged metallocene catalyst compound of structure (VII) includes two or more bridging groups (A). In one or more embodiments, (A) can be a divalent bridging group bound to both CpA and CpB selected from the group consisting of divalent C1 to C20 hydrocarbyls and C1 to C20 heteroatom containing hydrocarbonyls, where the heteroatom containing hydrocarbonyls include from one to three heteroatoms.

The bridging group (A) can include methylene, ethylene, ethylidene, propylidene, isopropylidene, diphenylmethylene, 1,2-dimethylethylene, 1,2-diphenylethylene, 1,1,2,2-tetramethylethylene, dimethylsilyl, diethylsilyl, methyl-ethylsilyl, trifluoromethylbutylsilyl, bis(trifluoromethyl)silyl, di(n-butyl)silyl, di(n-propyl)silyl, di(i-propyl)silyl, di(n-hexyl)silyl, dicyclohexylsilyl, diphenylsilyl, cyclohexylphenylsilyl, t-butylcyclohexylsilyl, di(t-butylphenyl)silyl, di(p-tolyl)silyl and the corresponding moieties where the Si atom is replaced by a Ge or a C atom; as well as dimethylsilyl, diethylsilyl, dimethylgermyl and diethylgermyl.

The bridging group (A) can also be cyclic, having, for example, 4 to 10 ring members; in a more particular exemplary embodiment, bridging group (A) can have 5 to 7 ring members. The ring members can be selected from the elements mentioned above, and, in a particular embodiment, can be selected from one or more of B, C, Si, Ge, N, and O. Non-limiting examples of ring structures which can be present as, or as part of, the bridging moiety are cyclobutylidene, cyclopentylidene, cyclohexylidene, cycloheptylidene, cyclooctylidene and the corresponding rings where one or two carbon atoms are replaced by at least one of Si, Ge, N and O. In one or more embodiments, one or two carbon atoms can be replaced by at least one of Si and Ge. The bonding arrangement between the ring and the Cp groups can be cis-, trans-, or a combination thereof.

The cyclic bridging groups (A) can be saturated or unsaturated and/or can carry one or more substituents and/or can be fused to one or more other ring structures. If present, the one or more substituents can be, in at least one specific embodiment, selected from the group consisting of hydrocarbyl (e.g., alkyl, such as methyl) and halogen (e.g., F, CO. The one or more Cp groups to which the above cyclic bridging moieties can optionally be fused can be saturated or unsaturated, and are selected from the group consisting of those having 4 to 10, more particularly 5, 6, or 7 ring members (selected from the group consisting of C, N, O, and S in a particular exemplary embodiment) such as, for example, cyclopentyl, cyclohexyl and phenyl. Moreover, these ring structures can themselves be fused such as, for example, in the case of a naphthyl group. Moreover, these (optionally fused) ring structures can carry one or more substituents. Illustrative, non-limiting examples of these substituents are hydrocarbyl (particularly alkyl) groups and halogen atoms. The ligands $Cp^A$ and $Cp^B$ of structure (VI) and (VII) can be different from each other. The ligands $Cp^A$ and $Cp^B$ of structure (VI) and (VII) can be the same. The metallocene catalyst compound can include bridged mono-ligand metallocene compounds (e.g., mono cyclopentadienyl catalyst components).

It is contemplated that the metallocene catalyst components discussed and described above include their structural or optical or enantiomeric isomers (racemic mixture), and, in one exemplary embodiment, can be a pure enantiomer. As used herein, a single, bridged, asymmetrically substituted metallocene catalyst compound having a racemic and/or meso isomer does not, itself, constitute at least two different bridged, metallocene catalyst components.

The catalyst system can include other single site catalysts such as Group 15-containing catalysts. The catalyst system can include one or more second catalysts in addition to the single site catalyst compound such as chromium-based catalysts, Ziegler-Natta catalysts, one or more additional single-site catalysts such as metallocenes or Group 15-containing catalysts, bimetallic catalysts, and mixed catalysts. The catalyst system can also include $AlCl_3$, cobalt, iron, palladium, or any combination thereof.

Group 15 Atom and Non-Metallocene Catalyst Compounds

The catalyst system can include one or more Group 15 metal-containing catalyst compounds. As used herein, these are termed non-metallocene catalyst compounds. The Group 15 metal-containing compound generally includes a Group 3 to 14 metal atom, a Group 3 to 7, or a Group 4 to 6 metal atom. In many embodiments, the Group 15 metal-containing compound includes a Group 4 metal atom bound to at least one leaving group and also bound to at least two Group 15 atoms, at least one of which is also bound to a Group 15 or 16 atom through another group.

In one or more embodiments, at least one of the Group 15 atoms is also bound to a Group 15 or 16 atom through another group which may be a C1 to C20 hydrocarbon group, a heteroatom containing group, silicon, germanium, tin, lead, or phosphorus, wherein the Group 15 or 16 atom may also be bound to nothing or a hydrogen, a Group 14 atom containing group, a halogen, or a heteroatom containing group, and wherein each of the two Group 15 atoms are also bound to a cyclic group and can optionally be bound to hydrogen, a halogen, a heteroatom or a hydrocarbyl group, or a heteroatom containing group.

The Group 15-containing metal compounds may be represented by a compound of any one of structures (VIII) or (IX):

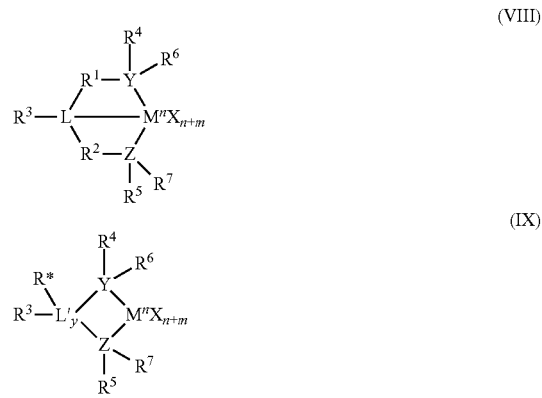

where M is a Group 3 to 12 transition metal or a Group 13 or 14 main group metal, a Group 4, 5, or 6 metal. In many embodiments, M is a Group 4 metal, such as zirconium, titanium, or hafnium. Each X is independently a leaving group, such as an anionic leaving group. The leaving group may include a hydrogen, a hydrocarbyl group, a heteroatom, a halogen, or an alkyl; y is 0 or 1 (when y is 0 group L' is absent). The term 'n' is the oxidation state of M. In various embodiments, n is +3, +4, or +5. In many embodiments, n is +4. The term 'm' represents the formal charge of the YZL or the YZL' ligand, and is 0, −1, −2 or −3 in various embodiments. In many embodiments, m is −2. L is a Group 15 or 16 element, such as nitrogen or oxygen; L' is a Group 15 or 16 element or Group 14 containing group, such as carbon, silicon or germanium. Y is a Group 15 element, such as nitrogen or phosphorus. In many embodiments, Y is nitrogen. Z is a Group 15 element, such as nitrogen or phosphorus. In many embodiments, Z is nitrogen. $R^1$ and $R^2$ are, independently, a $C_1$ to $C_{20}$ hydrocarbon group, a heteroatom containing group having up to twenty carbon atoms, silicon, germanium, tin, lead, or phosphorus. In many embodiments, $R^1$ and $R^2$ are a $C_2$ to $C_{20}$ alkyl, aryl or aralkyl group, such as a linear, branched or cyclic $C_2$ to $C_{20}$ alkyl group, or a $C_2$ to $C_6$ hydrocarbon group, such as the X described with respect to structures (VI) and (VII) above. $R^1$ and $R^2$ may also be interconnected to each other. $R^3$ may be absent or may be a hydrocarbon group, a hydrogen, a halogen, a heteroatom containing group. In many embodiments, $R^3$ is absent, for example, if L is an oxygen, or a hydrogen, or a linear, cyclic, or branched alkyl group having 1 to 20 carbon atoms. $R^4$ and $R^5$ are independently an alkyl group, an aryl group, substituted aryl group, a cyclic alkyl group, a substituted cyclic alkyl group, a cyclic aralkyl group, a substituted cyclic aralkyl group, or multiple ring system, often having up to 20 carbon atoms. In many embodiments, $R^4$ and $R^5$ have between 3 and 10 carbon atoms, or are a $C_1$ to $C_{20}$ hydrocarbon group, a $C_1$ to $C_{20}$ aryl group or a $C_1$ to $C_{20}$ aralkyl group, or a heteroatom containing group. $R^4$ and $R^5$ may be interconnected to each other. $R^6$ and $R^7$ are independently absent, hydrogen, an alkyl group, halogen, heteroatom, or a hydrocarbyl group, such as a linear, cyclic or branched alkyl group having 1 to 20 carbon atoms. In many embodiments, $R^6$ and $R^7$ are absent. R* may be absent, or may be a hydrogen, a Group 14 atom containing group, a halogen, or a heteroatom containing group.

By "formal charge of the YZL or YZL' ligand," it is meant the charge of the entire ligand absent the metal and the leaving groups X. By "$R^1$ and $R^2$ may also be interconnected" it is meant that R1 and R2 may be directly bound to each other or may be bound to each other through other groups. By "R4 and R5 may also be interconnected" it is meant that R4 and R5 may be directly bound to each other or may be bound to each other through other groups. An alkyl group may be linear, branched alkyl radicals, alkenyl radicals, alkynyl radicals, cycloalkyl radicals, aryl radicals, acyl radicals, aroyl radicals, alkoxy radicals, aryloxy radicals, alkylthio radicals, dialkylamino radicals, alkoxycarbonyl radicals, aryloxycarbonyl radicals, carbamoyl radicals, alkyl- or dialkyl-carbamoyl radicals, acyloxy radicals, acylamino radicals, aroylamino radicals, straight, branched or cyclic, alkylene radicals, or combination thereof. An aralkyl group is defined to be a substituted aryl group.

In one or more embodiments, R4 and R5 are independently a group represented by the following structure (X).

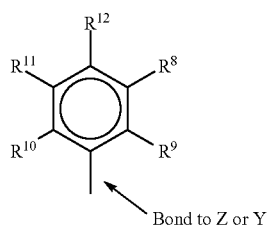

(X)

When $R^4$ and $R^5$ are as formula VII, $R^8$ to $R^{12}$ are each independently hydrogen, a $C_1$ to $C_{40}$ alkyl group, a halide, a heteroatom, a heteroatom containing group containing up to 40 carbon atoms. In many embodiments, $R^8$ to $R^{12}$ are a $C_1$ to $C_{20}$ linear or branched alkyl group, such as a methyl, ethyl, propyl, or butyl group. Any two of the R groups may form a cyclic group and/or a heterocyclic group. The cyclic groups may be aromatic. In one embodiment $R^9$, $R^{10}$ and $R^{12}$ are independently a methyl, ethyl, propyl, or butyl group (including all isomers). In another embodiment, $R^9$, $R^{10}$ and $R^{12}$ are methyl groups, and $R^8$ and $R^{11}$ are hydrogen.

In one or more embodiments, $R^4$ and $R^5$ are both a group represented by the following structure (XI).

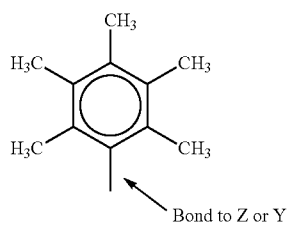

(XI)

When $R^4$ and $R^5$ follow structure (XI), M is a Group 4 metal, such as zirconium, titanium, or hafnium. In many embodiments, M is zirconium. Each of L, Y, and Z may be a nitrogen. Each of $R^1$ and $R^2$ may be —$CH_2$—$CH_2$—. $R^3$ may be hydrogen, and $R^6$ and $R^2$ may be absent. The Group 15 metal-containing catalyst compound can be represented by structure (IV). In formula IV, Ph represents phenyl.

Catalyst Forms

The catalyst system may include a catalyst component in a slurry, which may have an initial catalyst compound, and an added solution catalyst component that is added to the slurry. The initial catalyst component slurry may have no catalysts. In this case, two or more solution catalysts may be added to the slurry to cause each to be supported.

Any number of catalyst components may be used in embodiments. For example, the catalyst component slurry can include an activator and a support, or a supported activator. Further, the slurry can include a catalyst compound in addition to the activator and the support. As noted, the catalyst compound in the slurry may be supported.

The slurry may include one or more activators and supports, and one more catalyst compounds. For example, the slurry may include two or more activators (such as alumoxane and a modified alumoxane) and a catalyst compound, or the slurry may include a supported activator and more than one catalyst compounds. In one embodiment, the slurry includes a support, an activator, and two catalyst compounds. In another embodiment the slurry includes a support, an activator and two different catalyst compounds, which may be added to the slurry separately or in combination.

The molar ratio of metal in the activator to metal in the pre-catalyst compound in the slurry may be 1000:1 to 0.5:1, 300:1 to 1:1, or 150:1 to 1:1. The slurry can include a support material which may be any inert particulate carrier material known in the art, including, but not limited to, silica, fumed silica, alumina, clay, talc or other support materials such as disclosed above. In one embodiment, the slurry contains silica and an activator, such as methyl aluminoxane ("MAO") or modified methyl aluminoxane ("MMAO"), as discussed further below.

One or more diluents or carriers can be used to facilitate the combination of any two or more components of the catalyst system in the slurry or in the trim catalyst solution. For example, the single site catalyst compound and the activator can be combined together in the presence of toluene or another non-reactive hydrocarbon or hydrocarbon mixture to provide the catalyst mixture. In addition to toluene, other suitable diluents can include, but are not limited to, ethylbenzene, xylene, pentane, isopentane, hexane, isohexane, heptane, octane, other hydrocarbons, or any combination thereof. The support, either dry or mixed with toluene can then be added to the catalyst mixture or the catalyst/activator mixture can be added to the support.

The catalyst is not limited to a slurry arrangement, as a mixed catalyst system may be made on a support and dried. The dried catalyst system can then be fed to the reactor through a dry feed system.

Catalyst Supports

As used herein, the terms "support" and "carrier" are used interchangeably and refer to any support material, including a porous support material, such as talc, inorganic oxides, and inorganic chlorides. The one or more single site catalyst compounds of the slurry can be supported on the same or separate supports together with the activator, or the activator can be used in an unsupported form, or can be deposited on a support different from the single site catalyst compounds, or any combination thereof. This may be accomplished by any technique commonly used in the art. There are various other methods in the art for supporting a single site catalyst compound. For example, the single site catalyst compound can contain a polymer bound ligand. The single site catalyst compounds of the slurry can be spray dried. The support used with the single site catalyst compound can be functionalized, or with at least one substituent or leaving group is selected.

The support can be or include one or more inorganic oxides, for example, of Group 2, 3, 4, 5, 13, or 14 elements. The inorganic oxide can include, but is not limited to silica, alumina, titania, zirconia, boria, zinc oxide, magnesia, or any combination thereof. Illustrative combinations of inorganic oxides can include, but are not limited to, alumina-silica, silica-titania, alumina-silica-titania, alumina-zirconia, alumina-titania, and the like. The support can be or include silica, alumina, or a combination thereof. In one embodiment described herein, the support is silica.

Commercially available silica supports can include, but are not limited to, ES757, ES70, and ES70W available from PQ Corporation. Commercially available silica-alumina supports can include, but are not limited to, SIRAL® 1, SIRAL® 5, SIRAL® 10, SIRAL® 20, SIRAL® 28M, SIRAL® 30, and SIRAL® 40, available from SASOL®. Generally, catalyst supports comprising silica gels with activators, such as methylaluminoxanes (MAOs), are used in the trim systems described, since these supports may function better for co-supporting solution carried catalysts. Suitable supports may also be selected from the Cab-o-Sil® materials available from Cabot Corporation and silica materials available from the Grace division of W.R. Grace & Company.

Catalyst Activators

As used herein, the term "activator" may refer to any compound or combination of compounds, supported, or unsupported, which can activate a single site catalyst compound or component, such as by creating a cationic species of the catalyst component. For example, this can include the abstraction of at least one leaving group (the "X" group in the single site catalyst compounds described herein) from the metal center of the single site catalyst compound/component. The activator may also be referred to as a "co-catalyst".

For example, the activator can include a Lewis acid or a non-coordinating ionic activator or ionizing activator, or any other compound including Lewis bases, aluminum alkyls, and/or conventional-type co-catalysts. In addition to methylaluminoxane ("MAO") and modified methylaluminoxane ("MMAO") mentioned above, illustrative activators can include, but are not limited to, aluminoxane or modified aluminoxane, and/or ionizing compounds, neutral or ionic, such as tri (n-butyl)ammonium tetrakis(pentafluorophenyl) boron, a trisperfluorophenyl boron metalloid precursor, a trisperfluoronaphthyl boron metalloid precursor, or any combinations thereof.

It is recognized that these activators may or may not bind directly to the support surface or may be modified to allow them to be bound to a support surface while still maintaining their compatibility with the polymerization system. Such tethering agents may be derived from groups that are reactive with surface hydroxyl species. Non-limiting examples of reactive functional groups that can be used to create tethers include aluminum halides, aluminum hydrides, aluminum alkyls, aluminum aryls, aluminum alkoxides, electrophilic silicon reagents, alkoxy silanes, amino silanes, boranes.

Aluminoxanes can be described as oligomeric aluminum compounds having —Al(R)—O— subunits, where R is an alkyl group. Examples of aluminoxanes include, but are not limited to, methylaluminoxane ("MAO"), modified methylaluminoxane ("MMAO"), ethylaluminoxane, isobutylaluminoxane, or a combination thereof. Aluminoxanes can be produced by the hydrolysis of the respective trialkylaluminum compound. MMAO can be produced by the hydrolysis of trimethylaluminum and a higher trialkylaluminum, such as triisobutylaluminum. MMAOs are generally more soluble in aliphatic solvents and more stable during storage. There are a variety of methods for preparing aluminoxane and modified aluminoxanes.

As noted above, one or more organo-aluminum compounds such as one or more alkylaluminum compounds can be used in conjunction with the aluminoxanes. For example, alkylaluminum species that may be used are diethylaluminum ethoxide, diethylaluminum chloride, and/or diisobutylaluminum hydride. Examples of trialkylaluminum compounds include, but are not limited to, trimethylaluminum, triethylaluminum ("TEAL"), triisobutylaluminum ("TiBAl"), tri-n-hexylaluminum, tri-n-octylaluminum, tripropylaluminum, tributylaluminum, and the like.

Catalyst Component Solutions

The catalyst component solution may include only a catalyst compound, such as a metallocene, or may include an activator in addition to the catalyst compound. The catalyst solution used in the trim process can be prepared by dissolving the catalyst compound and optional activators in a liquid solvent. The liquid solvent may be an alkane, such as a C5 to C30 alkane, or a C5 to C10 alkane. Cyclic alkanes such as cyclohexane and aromatic compounds such as toluene may also be used. In addition, mineral oil may be used as a solvent. The solution employed should be liquid under the conditions of polymerization and relatively inert. In one embodiment, the liquid utilized in the catalyst compound solution is different from the diluent used in the catalyst component slurry. In another embodiment, the liquid utilized in the catalyst compound solution is the same as the diluent used in the catalyst component solution.

If the catalyst solution includes both activator and catalyst compound, the ratio of metal in the activator to metal in the catalyst compound in the solution may be 1000:1 to 0.5:1, 300:1 to 1:1, or 150:1 to 1:1. In various embodiments, the activator and catalyst compound are present in the solution at up to about 90 wt. %, at up to about 50 wt. %, at up to about 20 wt. %, preferably at up to about 10 wt. %, at up to about 5 wt. %, at less than 1 wt. %, or between 100 ppm and 1 wt. %, based upon the weight of the solvent and the activator or catalyst compound.

The catalyst component solution can include any one of the soluble catalyst compounds described in the catalyst section herein. As the catalyst is dissolved in the solution, a higher solubility is desirable. Accordingly, the catalyst compound in the catalyst component solution may often include a metallocene, which may have higher solubility than other catalysts.

In the polymerization process described below, any of the above described catalyst component containing solutions may be combined with any of the catalyst component containing slurry/slurries described above. In addition, more than one catalyst component solution may be utilized.

Continuity Additive/Static Control Agent

In gas-phase polyethylene production processes, it may be desirable to use one or more static control agents to aid in regulating static levels in the reactor. As used herein, a static control agent is a chemical composition which, when introduced into a fluidized bed reactor, may influence or drive the static charge (negatively, positively, or to zero) in the fluidized bed. The specific static control agent used may depend upon the nature of the static charge, and the choice of static control agent may vary dependent upon the polymer being produced and the single site catalyst compounds being used.

Control agents such as aluminum stearate may be employed. The static control agent used may be selected for its ability to receive the static charge in the fluidized bed without adversely affecting productivity. Other suitable static control agents may also include aluminum distearate, ethoxylated amines, and anti-static compositions such as those provided by Innospec Inc. under the trade name OCTASTAT. For example, OCTASTAT 2000 is a mixture of a polysulfone copolymer, a polymeric polyamine, and oil-soluble sulfonic acid.

The aforementioned control agents and other control agents or antistatic agents may be employed either alone or in combination as a control agent. For example, the carboxylate metal salt may be combined with an amine containing control agent (e.g., a carboxylate metal salt with any family member belonging to the KEMAMINE® (available from Crompton Corporation) or ATMER® (available from ICI Americas Inc.) family of products).

Other useful continuity additives include ethyleneimine additives useful in embodiments disclosed herein may include polyethyleneimines having the following general formula:

in which n may be from about 10 to about 10,000. The polyethyleneimines may be linear, branched, or hyperbranched (e.g., forming dendritic or arborescent polymer structures). They can be a homopolymer or copolymer of ethyleneimine or mixtures thereof (referred to as polyethyleneimine(s) hereafter). Although linear polymers represented by the chemical formula —[CH2-CH2-NH]— may be used as the polyethyleneimine, materials having primary, secondary, and tertiary branches can also be used. Commercial polyethyleneimine can be a compound having branches of the ethyleneimine polymer. Suitable polyethyleneimines are commercially available from BASF Corporation under the trade name Lupasol. These compounds can be prepared as a wide range of molecular weights and product activities. Examples of commercial polyethyleneimines sold by BASF suitable for use in the present invention include, but are not limited to, Lupasol FG and Lupasol WF.

Another useful continuity additive can include a mixture of aluminum distearate and an ethoxylated amine-type compound, e.g., IRGASTAT AS-990, available from Huntsman (formerly Ciba Specialty Chemicals). The mixture of aluminum distearate and ethoxylated amine type compound can be slurried in mineral oil e.g., Hydrobrite 380. For example, the mixture of aluminum distearate and an ethoxylated amine type compound can be slurried in mineral oil to have total slurry concentration of ranging from about 5 wt. % to about 50 wt. % or about 10 wt. % to about 40 wt. %, or about 15 wt. % to about 30 wt. %. Other static control agents and additives are contemplated.

The continuity additive(s) or static control agent(s) may be added to the reactor in an amount ranging from 0.05 to 200 ppm, based on the weight of all feeds to the reactor, excluding recycle. In some embodiments, the continuity additive may be added in an amount ranging from 2 to 100 ppm, or in an amount ranging from 4 to 50 ppm.

Gas Phase Polymerization Reactor

Figure 2:
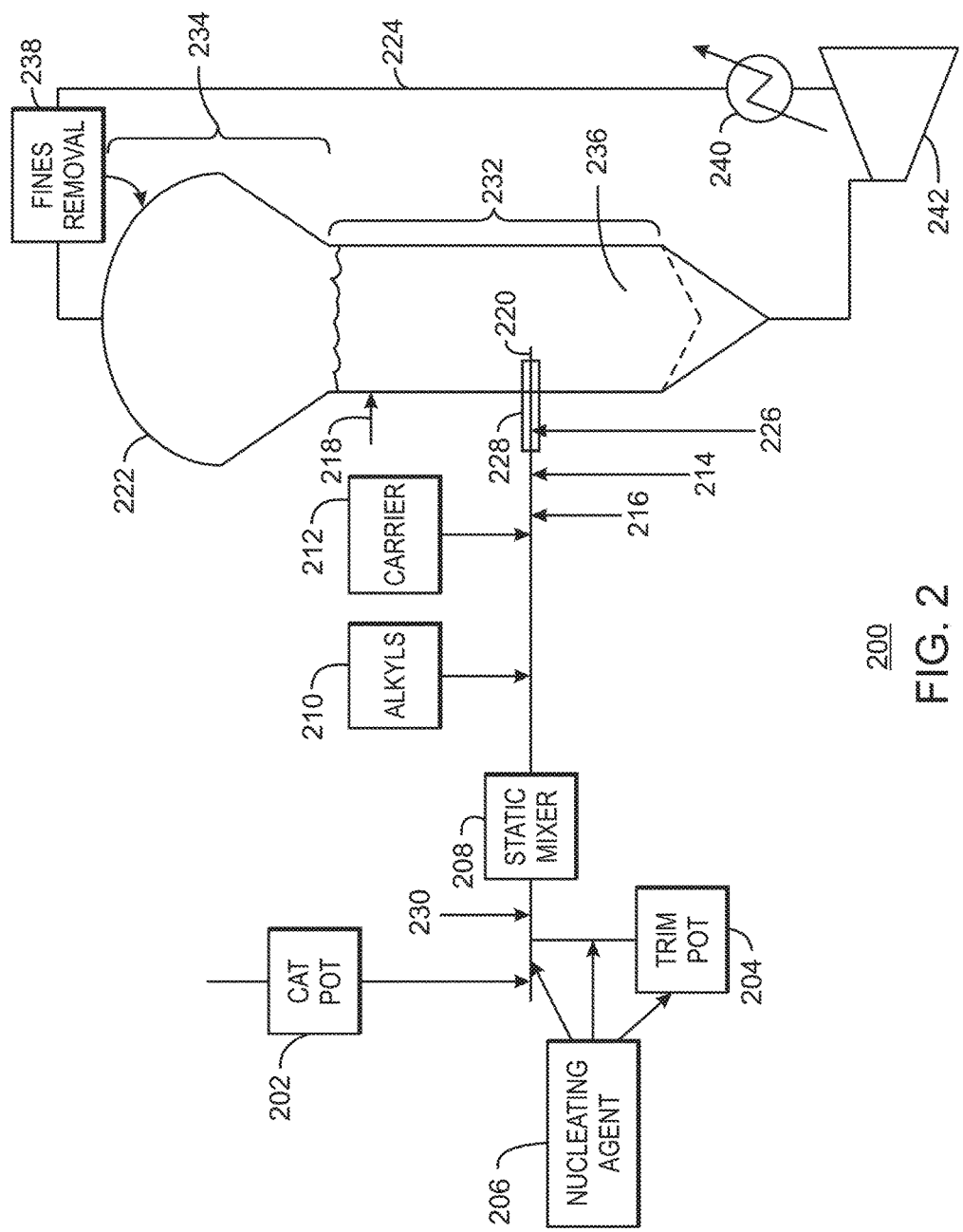
FIG. 2 is a schematic of a gas-phase reactor system, showing the addition of at least two catalysts, at least one of which is added as a trim catalyst in accordance with embodiments described herein.

FIG. 2 is a schematic of a gas-phase reactor system 200, showing the addition of at least two catalysts, at least one of which is added as a trim catalyst. The catalyst component slurry, preferably a mineral oil slurry including at least one support and at least one activator, at least one supported activator, and optional catalyst compounds may be placed in a vessel or catalyst pot (cat pot) 202. In one embodiment, the cat pot 202 is an agitated holding tank designed to keep the solids concentration homogenous. A catalyst component solution, prepared by mixing a solvent and at least one catalyst compound and/or activator, is placed in another vessel, which can be termed a trim pot 204. The catalyst component slurry can then be combined in-line with the catalyst component solution to form a final catalyst composition. A nucleating agent 206, such as silica, alumina, fumed silica or any other particulate matter may be added to the slurry and/or the solution in-line or in the vessels 202 or 204. Similarly, additional activators or catalyst compounds may be added in-line. For example, a second catalyst slurry that includes a different catalyst may be introduced from a second cat pot. The two catalyst slurries may be used as the catalyst system with or without the addition of a solution catalyst from the trim pot.

The catalyst component slurry and solution can be mixed in-line. For example, the solution and slurry may be mixed by utilizing a static mixer 208 or an agitating vessel (not shown). The mixing of the catalyst component slurry and the catalyst component solution should be long enough to allow the catalyst compound in the catalyst component solution to disperse in the catalyst component slurry such that the catalyst component, originally in the solution, migrates to the supported activator originally present in the slurry. The combination forms a uniform dispersion of catalyst compounds on the supported activator forming the catalyst composition. The length of time that the slurry and the solution are contacted is typically up to about 220 minutes, such as about 1 to about 60 minutes, about 5 to about 40 minutes, or about 10 to about 30 minutes.

When combining the catalysts, the activator and the optional support or additional co-catalysts, in the hydrocarbon solvents immediately prior to a polymerization reactor it is desirable that the combination yield a new polymerization catalyst in less than 1 h, less than 30 min, or less than 15 min. Shorter times are more effective, as the new catalyst is ready before being introduces into the reactor, providing the potential for faster flow rates.

In another embodiment, an aluminum alkyl, an ethoxylated aluminum alkyl, an aluminoxane, an anti-static agent or a borate activator, such as a C1 to C15 alkyl aluminum (for example tri-isobutyl aluminum, trimethyl aluminum or the like), a C1 to C15 ethoxylated alkyl aluminum or methyl aluminoxane, ethyl aluminoxane, isobutylaluminoxane, modified aluminoxane or the like are added to the mixture of the slurry and the solution in line. The alkyls, antistatic agents, borate activators and/or aluminoxanes may be added from an alkyl vessel 210 directly to the combination of the solution and the slurry, or may be added via an additional alkane (such as isopentane, hexane, heptane, and or octane) carrier stream, for example, from a hydrocarbon vessel 212. The additional alkyls, antistatic agents, borate activators and/or aluminoxanes may be present at up to about 500 ppm, at about 1 to about 300 ppm, at 10 to about 300 ppm, or at about 10 to about 100 ppm. Carrier streams that may be used include isopentane and or hexane, among others. The carrier may be added to the mixture of the slurry and the solution, typically at a rate of about 0.5 to about 60 lbs/hr (27 kg/hr). Likewise a carrier gas 214, such as nitrogen, argon, ethane, propane, and the like, may be added in-line to the mixture of the slurry and the solution. Typically the carrier gas may be added at the rate of about 1 to about 100 lb/hr (0.4 to 45 kg/hr), or about 1 to about 50 lb/hr (5 to 23 kg/hr), or about 1 to about 25 lb/hr (0.4 to 11 kg/hr).

In another embodiment, a liquid carrier stream is introduced into the combination of the solution and slurry that is moving in a downward direction. The mixture of the solution, the slurry and the liquid carrier stream may pass through a mixer or length of tube for mixing before being contacted with a gaseous carrier stream.

Similarly, a comonomer 216, such as hexene, another alpha-olefin, or diolefin, may be added in-line to the mixture of the slurry and the solution. The slurry/solution mixture is then passed through an injection tube 220 to a reactor 222. In some embodiments, the injection tube may aerosolize the slurry/solution mixture. Any number of tubing sizes and configurations may be used to aerosolize and/or inject the slurry/solution mixture.

In one embodiment, a gas stream 226, such as cycle gas, or re-cycle gas 224, monomer, nitrogen, or other materials is introduced into a support tube 228 that surrounds the injection tube 220. To assist in proper formation of particles in the reactor 222, a nucleating agent 218, such as fumed silica, can be added directly into the reactor 222.

When a metallocene catalyst or other similar catalyst is used in the gas phase reactor, oxygen or fluorobenzene can be added to the reactor 222 directly or to the gas stream 226 to control the polymerization rate. Thus, when a metallocene catalyst (which is sensitive to oxygen or fluorobenzene) is used in combination with another catalyst (that is not sensitive to oxygen) in a gas phase reactor, oxygen can be used to modify the metallocene polymerization rate relative to the polymerization rate of the other catalyst. An example of such a catalyst combination is bis(n-propyl cyclopentadienyl)zirconium dichloride and [(2,4,6-Me3C6H2)NCH2 CH2]2NHZrBn2, where Me is methyl, or bis(indenyl)zirconium dichloride and [(2,4,6-Me3C6H2)NCH2CH2] 2NHHfBn2, where Me is methyl. For example, if the oxygen concentration in the nitrogen feed is altered from 0.1 ppm to 0.5 ppm, significantly less polymer from the bisindenyl ZrCl2 will be produced and the relative amount of polymer produced from the [(2,4,6-Me3C6H2)NCH2CH2] 2NHHfBn2 is increased. The addition of water or carbon dioxide to gas phase polymerization reactors, for example, may be applicable for similar purposes. In one embodiment, the contact temperature of the slurry and the solution is in the range of from 0° C. to about 80° C., from about 0° C. to about 60° C., from about 10° C., to about 50° C., and from about 20° C. to about 40° C.

The example above is not limiting, as additional solutions and slurries may be included. For example, a slurry can be combined with two or more solutions having the same or different catalyst compounds and or activators. Likewise, the solution may be combined with two or more slurries each having the same or different supports, and the same or different catalyst compounds and or activators. Similarly, two or more slurries combined with two or more solutions, preferably in-line, where the slurries each comprise the same or different supports and may comprise the same or different catalyst compounds and or activators and the solutions comprise the same or different catalyst compounds and or activators. For example, the slurry may contain a supported activator and two different catalyst compounds, and two solutions, each containing one of the catalysts in the slurry, are each independently combined, in-line, with the slurry.

Use of Catalyst Composition to Control Product Properties

The properties of the product polymer may be controlled by adjusting the timing, temperature, concentrations, and sequence of the mixing of the solution, the slurry and any optional added materials (nucleating agents, catalyst compounds, activators, etc) described above. The MWD, melt index, relative amount of polymer produced by each catalyst, and other properties of the polymer produced may also be changed by manipulating process parameters. Any number of process parameters may be adjusted, including manipulating hydrogen concentration in the polymerization system, changing the amount of the first catalyst in the polymerization system, changing the amount of the second catalyst in the polymerization system. Other process parameters that can be adjusted include changing the relative ratio of the catalyst in the polymerization process (and optionally adjusting their individual feed rates to maintain a steady or constant polymer production rate). The concentrations of reactants in the reactor 222 can be adjusted by changing the amount of liquid or gas that is withdrawn or purged from the process, changing the amount and/or composition of a recovered liquid and/or recovered gas returned to the polymerization process, wherein the recovered liquid or recovered gas can be recovered from polymer discharged from the polymerization process. Further concentration parameters that can be adjusted include changing the polymerization temperature, changing the ethylene partial pressure in the polymerization process, changing the ethylene to comonomer ratio in the polymerization process, changing the activator to transition metal ratio in the activation sequence. Time dependent parameters may be adjusted, such as changing the relative feed rates of the slurry or solution, changing the mixing time, the temperature and or degree of mixing of the slurry and the solution in-line, adding different types of activator compounds to the polymerization process, and adding oxygen or fluorobenzene or other catalyst poison to the polymerization process. Any combinations of these adjustments may be used to control the properties of the final polymer product.

In one embodiment, the MWD of the polymer product is measured at regular intervals and one of the above process parameters, such as temperature, catalyst compound feed rate, the ratios of the two or more catalysts to each other, the ratio of comonomer to monomer, the monomer partial pressure, and or hydrogen concentration, is altered to bring the composition to the desired level, if necessary. The MWD may be measured by size exclusion chromatography (SEC), e.g., gel permeation chromatography (GPC), among other techniques.

In one embodiment, a polymer product property is measured in-line and in response the ratio of the catalysts being combined is altered. In one embodiment, the molar ratio of the catalyst compound in the catalyst component slurry to the catalyst compound in the catalyst component solution, after the slurry and solution have been mixed to form the final catalyst composition, is 500:1 to 1:500, or 100:1 to 1:100, or 50:1 to 1:50 or 40:1 to 1:10. In another embodiment, the molar ratio of a Group 15 catalyst compound in the slurry to a ligand metallocene catalyst compound in the solution, after the slurry and solution have been mixed to form the catalyst composition, is 500:1, 100:1, 50:1, 10:1, or 5:1. The product property measured can include the dynamic shear viscosity, flow index, melt index, density, MWD, comonomer content, and combinations thereof. In another embodiment, when the ratio of the catalyst compounds is altered, the introduction rate of the catalyst composition to the reactor, or other process parameters, is altered to maintain a desired production rate.

Polymerization Process

The catalyst system can be used to polymerize one or more olefins to provide one or more polymer products therefrom. Any suitable polymerization process can be used, including, but not limited to, high pressure, solution, slurry, and/or gas phase polymerization processes. In embodiments that use other techniques besides gas phase polymerization, modifications to a catalyst addition system that are similar to those discussed with respect to FIG. 2 can be used. For example, a trim system may be used to feed catalyst to a loop slurry reactor for polyethylene copolymer production.

The terms "polyethylene" and "polyethylene copolymer" refer to a polymer having at least 50 wt. % ethylene-derived units. In various embodiments, the polyethylene can have at least 70 wt. % ethylene-derived units, at least 80 wt. % ethylene-derived units, at least 90 wt. % ethylene-derived units, or at least 95 wt. % ethylene-derived units. The polyethylene polymers described herein are generally copolymer, but may also include terpolymers, having one or more other monomeric units. As described herein, a polyethylene can include, for example, at least one or more other olefins or comonomers. Suitable comonomers can contain 3 to 16 carbon atoms, from 3 to 12 carbon atoms, from 4 to 10 carbon atoms, and from 4 to 8 carbon atoms. Examples of comonomers include, but are not limited to, propylene, 1-butene, 1-pentene, 1-hexene, 1-heptene, 1-octene, 4-methylpent-1-ene, 1-decene, 1-dodecene, 1-hexadecene, and the like. Additionally, small amounts of diene monomers, such as 1,7-octadiene may be added to the polymerization to adjust polymer properties.

Referring again to FIG. 2, the fluidized bed reactor 222 can include a reaction zone 232 and a velocity reduction zone 234. The reaction zone 232 can include a bed 236 that includes growing polymer particles, formed polymer particles and a minor amount of catalyst particles fluidized by the continuous flow of the gaseous monomer and diluent to remove heat of polymerization through the reaction zone. Optionally, some of the re-circulated gases 224 can be cooled and compressed to form liquids that increase the heat removal capacity of the circulating gas stream when readmitted to the reaction zone. A suitable rate of gas flow can be readily determined by experimentation. Make-up of gaseous monomer to the circulating gas stream can be at a rate equal to the rate at which particulate polymer product and monomer associated therewith is withdrawn from the reactor and the composition of the gas passing through the reactor can be adjusted to maintain an essentially steady state gaseous composition within the reaction zone. The gas leaving the reaction zone 232 can be passed to the velocity reduction zone 234 where entrained particles are removed, for example, by slowing and falling back to the reaction zone 232. If desired, finer entrained particles and dust can be removed in a separation system 238, such as a cyclone and/or fines filter. The gas 224 can be passed through a heat exchanger 240 where at least a portion of the heat of polymerization can be removed. The gas can then be compressed in a compressor 242 and returned to the reaction zone 232.

The reactor temperature of the fluid bed process can be greater than about 30° C., about 40° C., about 50° C., about 90° C., about 100° C., about 110° C., about 120° C., about 150° C., or higher. In general, the reactor temperature is operated at the highest feasible temperature taking into account the sintering temperature of the polymer product within the reactor. Thus, the upper temperature limit in one embodiment is the melting temperature of the polyethylene copolymer produced in the reactor. However, higher temperatures may result in narrower MWDs, which can be improved by the addition of structure (IV), or other co-catalysts, as described herein.

Hydrogen gas can be used in olefin polymerization to control the final properties of the polyolefin. Using certain catalyst systems, increasing concentrations (partial pressures) of hydrogen can increase the flow index (FI), or melt index (MI) of the polyethylene copolymer generated. The flow index can thus be influenced by the hydrogen concentration. The amount of hydrogen in the polymerization can be expressed as a mole ratio relative to the total polymerizable monomer, for example, ethylene, or a blend of ethylene and hexene or propylene.

The amount of hydrogen used in the polymerization process can be an amount necessary to achieve the desired flow index of the final polyolefin polymer. For example, the mole ratio of hydrogen to total monomer (H2:monomer) can be greater than about 0.0001, greater than about 0.0005, or greater than about 0.001. Further, the mole ratio of hydrogen to total monomer (H2:monomer) can be less than about 10, less than about 5, less than about 3, and less than about 0.10. A desirable range for the mole ratio of hydrogen to monomer can include any combination of any upper mole ratio limit with any lower mole ratio limit described herein. Expressed another way, the amount of hydrogen in the reactor at any time can range to up to about 5,000 ppm, up to about 4,000 ppm in another embodiment, up to about 3,000 ppm, or between about 50 ppm and 5,000 ppm, or between about 50 ppm and 2,000 ppm in another embodiment. The amount of hydrogen in the reactor can range from a low of about 1 ppm, about 50 ppm, or about 100 ppm to a high of about 400 ppm, about 800 ppm, about 1,000 ppm, about 1,500 ppm, or about 2,000 ppm, based on weight. Further, the ratio of hydrogen to total monomer (H2:monomer) can be about 0.00001:1 to about 2:1, about 0.005:1 to about 1.5:1, or about 0.0001:1 to about 1:1. The one or more reactor pressures in a gas phase process (either single stage or two or more stages) can vary from 690 kPa (100 psig) to 3,448 kPa (500 psig), in the range from 1,379 kPa (200 psig) to 2,759 kPa (400 psig), or in the range from 1,724 kPa (250 psig) to 2,414 kPa (350 psig).

The gas phase reactor can be capable of producing from about 10 kg of polymer per hour (25 lbs/hr) to about 90,900 kg/hr (200,000 lbs/hr), or greater, and greater than about 455 kg/hr (1,000 lbs/hr), greater than about 4,540 kg/hr (10,000 lbs/hr), greater than about 11,300 kg/hr (25,000 lbs/hr), greater than about 15,900 kg/hr (35,000 lbs/hr), and greater than about 22,700 kg/hr (50,000 lbs/hr), and from about 29,000 kg/hr (65,000 lbs/hr) to about 45,500 kg/hr (100,000 lbs/hr).

As noted, a slurry polymerization process can also be used in embodiments. A slurry polymerization process generally uses pressures in the range of from about 101 kPa (1 atmosphere) to about 5,070 kPa (50 atmospheres) or greater, and temperatures in the range of from about 0° C. to about 120° C., and more particularly from about 30° C. to about 100° C. In a slurry polymerization, a suspension of solid, particulate polymer can be formed in a liquid polymerization diluent medium to which ethylene, comonomers, and hydrogen along with catalyst can be added. The suspension including diluent can be intermittently or continuously removed from the reactor where the volatile components are separated from the polymer and recycled, optionally after a distillation, to the reactor. The liquid diluent employed in the polymerization medium can be an alkane having from 3 to 7 carbon atoms, such as, for example, a branched alkane. The medium employed should be liquid under the conditions of polymerization and relatively inert. When a propane medium is used the process should be operated above the reaction diluent critical temperature and pressure. In one embodiment, a hexane, isopentane, or isobutane medium can be employed. The slurry can be circulated in a continuous loop system.

The product polyethylene can have a melt flow ratio (MFR) or melt index ratio (MIR), I21/I2, ranging from about 10 to less than about 300, or, in many embodiments, from about 25 to about 80. Flow index (FI, HLMI, or I21) can be measured in accordance with ASTM D1238 (190° C., 21.6 kg). Melt index (MI, I2) can be measured in accordance with ASTM D1238 (at 190° C., 2.16 kg weight).

Density can be determined in accordance with ASTM D-792. Density is expressed as grams per cubic centimeter (g/cm3) unless otherwise noted. The polyethylene can have a density ranging from a low of about 0.89 g/cm3, about 0.90 g/cm3, or about 0.91 g/cm3 to a high of about 0.95 g/cm3, about 0.96 g/cm3, or about 0.97 g/cm3. The polyethylene can have a bulk density, measured in accordance with ASTM D1895 method B, of from about 0.25 g/cm3 to about 0.5 g/cm3. For example, the bulk density of the polyethylene can range from a low of about 0.30 g/cm3, about 0.32 g/cm3, or about 0.33 g/cm3 to a high of about 0.40 g/cm3, about 0.44 g/cm3, or about 0.48 g/cm3.

Gel count was determined herein using an optical control system of model ME-20/2800 extruder, a CR9 chill roll and winder unit, and FSA-100 film analyzer, available from Optical Control Systems (OCS) GmbH of Germany. The system consisted of a ¾ inch screw and 6 inch fixed lip. The screw speed was 50 rpm, with a temperature profile of 190, 220, 215, 215, and 215° C., a chill roll temperature of 30° C., and a take off speed of about 3.0 m/min to produce a film of 50 μm.

The polyethylene can be suitable for such articles as films, fibers, nonwoven and/or woven fabrics, extruded articles, and/or molded articles. Examples of films include blown or cast films formed in single layer extrusion, coextrusion, or lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications, agricultural films and sheets. Examples of fibers include melt spinning, solution spinning and melt blown fiber operations for use in woven or non-woven form to make filters, diaper fabrics, hygiene products, medical garments, geotextiles, etc. Examples of extruded articles include tubing, medical tubing, wire and cable coatings, pipe, geomembranes, and pond liners. Examples of molded articles include single and multi-layered constructions by injection molding or rotation molding or blow molding processes in the form of bottles, tanks, large hollow articles, rigid food containers and toys, etc.

EXAMPLES

A gas phase fluidized bed reactor of 0.35 meters internal diameter and 2.3 meters in bed height was utilized for all of the polymerizations. The fluidized bed was made up of polymer granules and gaseous feed streams of ethylene and hydrogen together with liquid 1-hexene comonomer were introduced below the reactor bed into the recycle gas line. The individual flow rates of ethylene, hydrogen and 1-hexene were controlled to maintain fixed composition targets. The ethylene concentration was controlled to maintain a constant ethylene partial pressure. The hydrogen was controlled to maintain constant hydrogen to ethylene mole ratio. The concentrations of all the gases were measured by an on-line gas chromatograph to ensure relatively constant composition in the recycle gas stream. The reacting bed of growing polymer particles was maintained in a fluidized state by the continuous flow of the make-up feed and recycle gas through the reaction zone. A superficial gas velocity of 0.6-0.9 meters/sec was used to achieve this. The fluidized bed was maintained at a constant height by withdrawing a portion of the bed at a rate equal to the rate of formation of particulate product. The polymer production rate was in the range of 15-25 kg/hour. The product was removed semi-continuously via a series of valves into a fixed volume chamber. This product was purged to remove entrained hydrocarbons and treated with a small stream of humidified nitrogen to deactivate any trace quantities of residual catalyst and cocatalyst.

The solid catalyst was dispersed in degassed and dried mineral oil as a nominal 18 wt % slurry and contacted with the trim catalyst solution for a few seconds to minutes before being injected directly into the fluidized bed using purified nitrogen and isopentane as carriers in a manner that produces an effervescence of nitrogen in the liquid and spray to aid in dispersing the catalyst. The trim catalyst was provided initially as a solution, and substantially diluted with isopentane to a concentration of about 0.02 wt % or 0.04 wt % before being mixed in-line with the slurry catalyst component in a continuous manner prior to injection to the reactor. The relative feeds of the slurry catalyst and the trim catalyst were controlled to achieve an aim target feed ratio of their active polymerization metals, and the feeds adjusted accordingly for overall polymer production rate and the relative amounts of polymer produced by each catalyst based somewhat on polymer flow index MFR and density, while also manipulating reaction temperature and the gas compositions in the reactor. The reacting bed of growing polymer particles was maintained in a fluidized state by continually flowing the makeup feed and recycle gas through the reaction zone at a superficial gas velocity in about the range of 2.0 to 2.2 ft/sec (0.61 to 0.67 m/sec). The reactor was operated at a total pressure of about 350 psig (2413 kPa gauge). To maintain a constant fluidized bed temperature in the reactor, the temperature of the recycle gas was continuously adjusted up or down by passing the recirculating gas through the tubes of a shell-and-tube heat exchanger with cooling water on the shell-side to accommodate any changes in the rate of heat generation due to the polymerization.

A slurry mixture of continuity additive in degassed and dried mineral oil (1:1 Aluminum stearate:N-nonyldiethanolamine at 20 wt % concentration) was fed into the reactor using a mixture of isopentane and nitrogen.

Catalyst Preparation

All procedures were performed under nitrogen, with the exclusion of air and moisture. The combined Hf and Zr loading for all of the cosupported mixed metallocene catalysts was about 30 μmol (Zr+Hf)/g of catalyst, and the aluminum loading was about 4.5 mmol Al/g of catalyst. For these cosupported mixed metallocene catalysts, the HfP/EtInd ratios used for the catalyst preparation include 85:15, 60:40, and 50:50, on a mole fraction basis, as shown below. The methylaluminoxane (MAO, Albemarle 10 wt %) and the metallocenes were added to a reactor first and mixed for half an hour at room temperature. Silica (ES757, PQ Corp. calcined at 875° C.) was then added directly into the MAO/metallocenes solution and mixed for an additional one hour at room temperature. The catalysts were then dried under vacuum until the internal temperature was lined out at ~70° C. for 2.5 hours. The single component catalyst used in Example 1 was prepared in a manner similar to that described above for the mixed metallocene catalysts. The Hf loading for this catalyst was about 0.045 mmol Hf/g of catalyst and the aluminum loading for this catalyst was about 4.5 mmol Al/g of catalyst. In each case, a catalyst slurry was made by adding the dry solid catalyst to Hydrobrite 380 mineral oil to form an 18 wt % slurry.

For preparation of the trim solution, the appropriate metallocene was dissolved in dry, degassed isopentane. The trim solution concentration of metallocene was 0.02 wt % for Examples 1, 2 and 4. The trim solution concentration of metallocene was 0.04 wt % for Example 5.

In Example 1, the catalyst system comprised a supported single component HfP catalyst with EtInd added as trim.

In Example 2, the catalyst system comprised cosupported HfP and EthInd catalysts, with an initial co-deposit on a mol fraction basis of 0.85 HfP and 0.15 EthInd. Additional EthInd slurry was added as catalyst trim.

In Example 3, the catalyst system comprised cosupported HfP and EthInd catalysts, with an initial co-deposit on a mol fraction basis was 0.60 HfP and 0.40 EthInd. There was no trim catalyst.

In Example 4, the catalyst system comprised cosupported HfP and EthInd catalysts, with an initial co-deposit on a mol fraction basis of 0.60 EthInd and 0.40 HfP. Additional HfP slurry was added as catalyst trim.

In Example 5, the catalyst system comprised cosupported HfP and EthInd catalysts, with an initial co-deposit on a mol fraction basis of 0.50 EthInd and 0.50 HfP. Additional HfP slurry was added as catalyst trim.

Table 1 below summarizes polymerization reaction data for each of Examples 1-5.

TABLE 1

Polymerization Reaction Data for Examples 1-5

| | Example | | | | |
|---|---|---|---|---|---|
| | 1 | 2 | 3 | 4 | 5 |
| C2 partial pressure, psia | 207.6 | 220.1 | 220.0 | 220.0 | 219.9 |
| C6/C2 molar ratio | 0.0193 | 0.0215 | 0.0279 | 0.0238 | 0.0270 |
| H2/C2 ratio, ppmv/mole % | 8.14 | 7.96 | 7.01 | 7.00 | 6.50 |
| Reactor temp, ° C. | 80 | 80 | 80 | 80 | 80 |
| Continuity additive, ppmw | 27.30 | 27.30 | 31.19 | 30.86 | 28.94 |
| Hf/Zr molar feed ratio | 2.72 | 1.82 | 1.45 | 2.86 | 7.27 |
| Residence time, hours | 2.53 | 2.62 | 3.27 | 2.79 | 2.78 |
| Slurry catalyst flow rate, mL/hour | 13.3 | 15.3 | 17.5 | 17.6 | 16.0 |
| Trim Flow, g/hour | 0.01414 | 0.00875 | 0 | 0.01995 | 0.11653 |

Table 2 below summarizes catalyst loading data for the catalysts used in each of Examples 1-5. The catalyst loading is provided in µmol/g of the solid dry catalyst.

TABLE 2

Catalyst Loading for Examples 1-5

| | Example | | | | |
|---|---|---|---|---|---|
| | 1 | 2 | 3 | 4 | 5 |
| Catalyst Hf Loading, µmol/g | 43.7 | 24.8 | 17 | 17 | 15.7 |
| Catalyst Zr Loading µmol/g | 0 | 4.9 | 11.7 | 11.7 | 16.8 |
| Initial Hf/Zr ratio (mol/mol) | NA | 5 | 1.4 | 1.4 | 0.9 |
| Final Hf/Zr ratio (mol/mol) | 2.7 | 1.8 | 1.4 | 2.9 | 7.3 |

Table 3 below provides polymer characteristics for the polymers produced in Examples 1-5, as well as gel data measured as described above for the extruded polymers. This gel data is 1$^{st}$ pass data for samples extruded on two different extruders: a Werner & Pfleiderer 57 mm Twin Screw Extruder ("WP-57"), and a Werner & Pfleiderer 30 mm Twin Screw Extruder ("WP-30"). The WP-57 is a co-rotating twin screw extruder, with an L/D ratio of 24:1 and an underwater pelletizer. The WP-30 is a co-rotating twin screw extruder with an L/D ratio of 29:1 and an underwater pelletizer.

TABLE 3

Polymer Characteristics and Gel Data for Examples 1-5

| | Example | | | | |
|---|---|---|---|---|---|
| | 1 | 2 | 3 | 4 | 5 |
| | HfP LMW-Trim | CD 85:15 LMW-Trim | CD 60:40 No Trim | CD 60:40 HMW-Trim | CD 50:50 HMW-Trim |
| Resin Characteristics | | | | | |
| Density (g/cm3) | 0.920 | 0.921 | 0.921 | 0.922 | 0.921 |
| MI (dg/min) | 0.8 | 0.9 | 1.1 | 1.1 | 1.0 |
| MFR (I-21/I-2) | 50 | 49 | 60 | 49 | 58 |
| OCS (gels per ppm in extruded resin) | | | | | |
| TDA @ 1st Pass on WP-57 | 11,430 | 4,626 | 221 | 100 | 68 |
| TDA @ 1st Pass on WP-30 | 3,492 | 263 | 38 | 33 | 16 |

Figure 3:
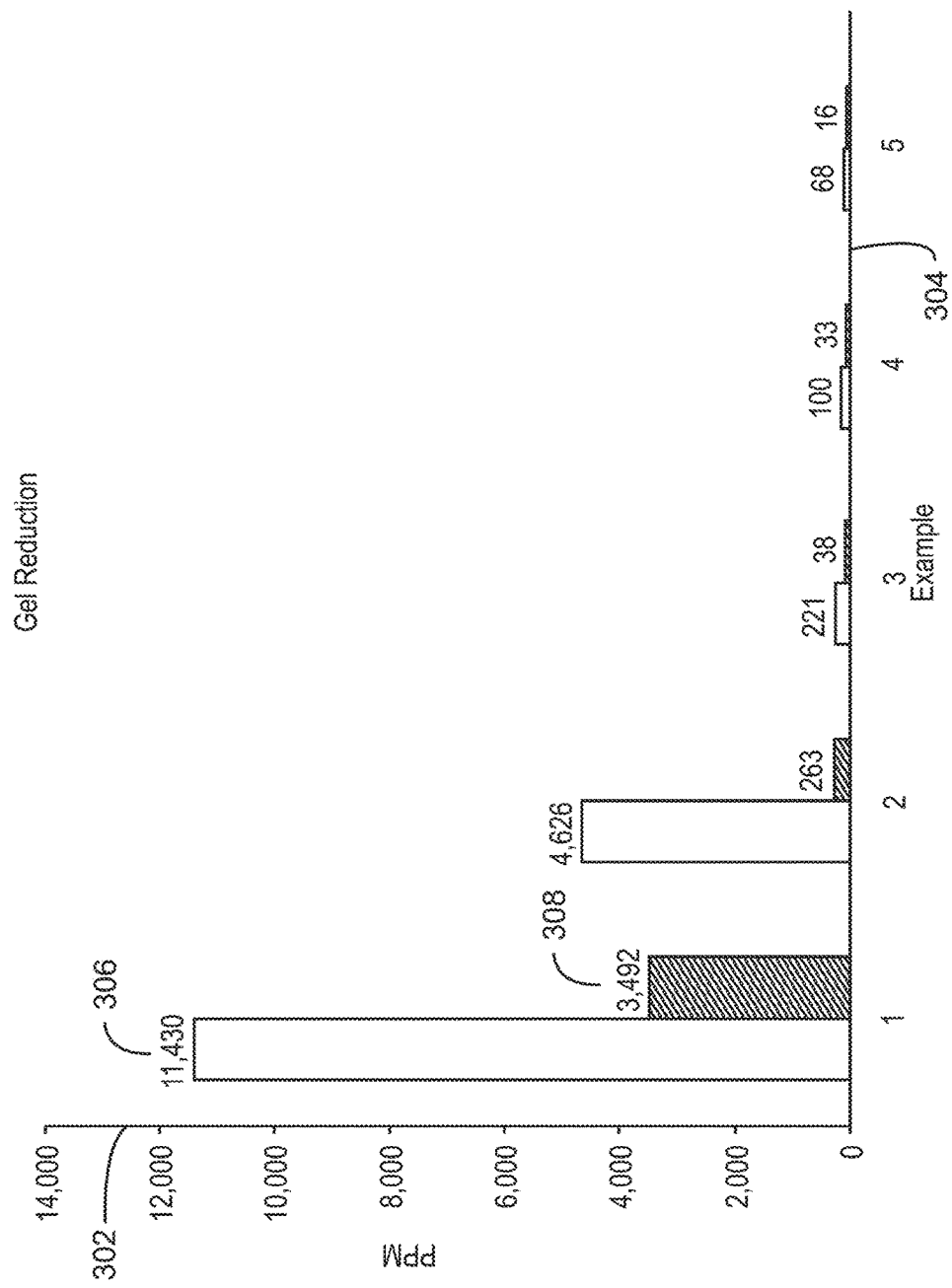
FIG. 3 is an exemplary bar chart depicting gel data of polyethylene polymerized via different catalyst systems processed on two different extruders.

The presence of gels in the polyethylene was significantly lower in Examples 4 and 5 versus Examples 1-3. FIG. 3 is a bar chart 300 depicting the 1st-pass gel data shown in Table 3. The vertical axis 302 is gels part per million (ppm) of the polyethylene, as shown in Table 3. The horizontal axis 304 is the Example numbers. The first bar in each Example is for the 1st pass on a Werner & Pfleiderer 57 mm Twin Screw Extruder ("WP-57"). The second bar in each Example is for the 1st pass on a Werner & Pfleiderer ("WP-30") 30 mm Twin Screw Extruder. The first bar in Example 1 is labeled with the reference numeral 306. The second bar in Example 1 is labeled with the reference numeral 308. As can be seen from Table 3 and FIG. 3, a significant reduction in gels is realized in embodiments of the present techniques.

All numerical values are "about" or "approximately" the indicated value, and take into account experimental error and variations that would be expected by a person having ordinary skill in the art. Further, various terms have been defined above. To the extent a term used in a claim is not defined above, it should be given the broadest definition persons in the pertinent art have given that term as reflected in at least one printed publication or issued patent. All patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention can be devised without departing from the basic scope thereof, and the scope thereof is determined by the claims that follow.

What is claimed is:

1. A method of polymerizing olefins, comprising:
   contacting ethylene and at least one comonomer with a catalyst system to produce a polyolefin polymer that is multimodal, the catalyst system comprising a first catalyst that promotes polymerization of the ethylene into a low molecular weight (LMW) portion of the polyolefin polymer, and a second catalyst that promotes polymerization of the ethylene into a high molecular weight (HMW) portion of the polyolefin polymer;
   wherein the first catalyst and at least a portion of the second catalyst are co-supported to form a commonly-supported catalyst system; and
   wherein at least a portion of the second catalyst is added as a catalyst trim feed to the catalyst system, wherein a molar amount of the second catalyst added via the catalyst trim feed per gram of a dry commonly-supported catalyst system ranges from 1.8 µmol to 150 µmol, wherein the first catalyst comprises di(1-ethyl-indenyl) zirconium dimethyl having at least one of the following structures:

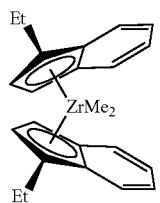

-continued

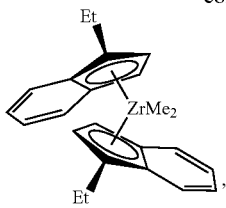

or di(1-ethylindenyl) zirconium dichloride having one of the structures above except that the Me is replaced by Cl, and wherein the second catalyst comprises bis(n-propylcyclopentadienyl) hafnium dimethyl having the following structure:

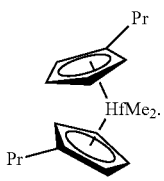

2. The method of claim 1, wherein the commonly-supported catalyst system comprises at least one catalyst having the following structure:

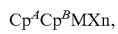

wherein $Cp^A$ and $Cp^B$ are each independently selected from the group consisting of substituted or unsubstituted cyclopentadienyl, indenyl, tetrahydroindenyl, and fluorenyl compounds;

wherein M is chemically bonded to $Cp^A$ and $Cp^B$ and selected from the group consisting of Groups 4, 5, and 6 atoms;

wherein each X is chemically bonded to M and is independently selected from the group consisting of halogen ions, hydrides, C1 to C12 alkyls, C2 to C12 alkenyls, C6 to C12 aryls, C7 to C20 alkylaryls, C1 to C12 alkoxys, C6 to C16 aryloxys, C7 to C8 alkylaryloxys, C1 to C12 fluoroalkyls, C6 to C12 fluoroaryls, and C1 to C12 heteroatom-containing hydrocarbons; and wherein n is 0 or an integer from 1 to 4.

3. The method of claim 1, wherein the commonly-supported catalyst system comprises at least one catalyst that is a chromium-based catalyst, Ziegler-Natta catalyst, or Group 15-containing catalyst.

4. The method of claim 1, wherein the catalyst trim feed is added to a slurry comprising the first catalyst.

5. The method of claim 1, wherein the catalyst trim feed is a solution trim feed.

6. The method of claim 1, wherein the molar amount of catalyst added via the catalyst trim feed per gram of the dry commonly-supported catalyst system ranges from 12.4 μmol to 75 μmol.

7. The method of claim 1, wherein the polyolefin polymer is bimodal.

8. The method of claim 1, wherein the commonly-supported catalyst system comprises an activator.

9. The method of claim 8, wherein the activator comprises at least one of a methylaluminoxane (MAO) and a silica methylaluminoxane (SMAO).

10. The method of claim 1, wherein the initial co-deposit on a mol fraction basis of the second catalyst to the first catalyst in the commonly-supported catalyst system ranges from about 0.7:0.3 to about 0.3:0.7.

11. The method of claim 1, wherein the initial co-deposit on a mol fraction basis of the second catalyst to the first catalyst in the commonly-supported catalyst system ranges from about 0.6:0.4 to about 0.4:0.6.

12. The method of claim 1, wherein the comonomer comprises an alpha olefin having from 4 to 20 carbon atoms.

13. The method of claim 1, wherein the comonomer comprises butene or hexene.

* * * * *